US012110351B2

(12) United States Patent
Hartnagel et al.

(10) Patent No.: US 12,110,351 B2
(45) Date of Patent: Oct. 8, 2024

(54) METHOD FOR THE PRODUCTION OF SUPERABSORBERS

(71) Applicant: BASF SE, Ludwigshafen (DE)

(72) Inventors: Kristine Hartnagel, Ludwigshafen (DE); Thomas Gieger, Ludwigshafen (DE); Thomas Daniel, Ludwigshafen (DE); Marcus Schroeder, Ludwigshafen (DE); Michelle Morano, Charlotte, NC (US); Nathaniel Troy Greene, Charlotte, NC (US)

(73) Assignee: BASF SE, Ludwigshafen (DE)

( * ) Notice: Subject to any disclaimer, the term of this patent is extended or adjusted under 35 U.S.C. 154(b) by 288 days.

(21) Appl. No.: 17/717,598

(22) Filed: Apr. 11, 2022

(65) Prior Publication Data

US 2022/0235152 A1 Jul. 28, 2022

Related U.S. Application Data

(63) Continuation of application No. 16/321,638, filed as application No. PCT/EP2017/069446 on Aug. 1, 2017, now Pat. No. 11,325,990.

(30) Foreign Application Priority Data

Aug. 10, 2016 (EP) ..................... 16183579

(51) Int. Cl.
| | |
|---|---|
| C08F 2/22 | (2006.01) |
| A61L 15/60 | (2006.01) |
| B01J 20/26 | (2006.01) |
| B01J 20/28 | (2006.01) |
| C08F 2/01 | (2006.01) |
| C08F 2/44 | (2006.01) |
| C08F 6/14 | (2006.01) |
| C08F 220/06 | (2006.01) |
| C08J 3/12 | (2006.01) |
| C08J 3/24 | (2006.01) |
| C08K 3/011 | (2018.01) |
| C08K 3/30 | (2006.01) |
| C08K 5/5317 | (2006.01) |

(52) U.S. Cl.
CPC ............... *C08F 2/22* (2013.01); *A61L 15/60* (2013.01); *B01J 20/261* (2013.01); *B01J 20/28047* (2013.01); *C08F 2/01* (2013.01); *C08F 2/44* (2013.01); *C08F 6/14* (2013.01); *C08F 220/06* (2013.01); *C08J 3/12* (2013.01); *C08J 3/245* (2013.01); *C08K 3/011* (2018.01); *C08K 3/30* (2013.01); *C08K 5/5317* (2013.01); *B01J 2220/68* (2013.01); *C08J 2333/02* (2013.01); *C08K 2003/3081* (2013.01)

(58) Field of Classification Search
CPC ...... C08F 2/22; C08F 2/01; C08F 2/44; C08F 6/14; C08F 220/06; C08K 3/011; C08K 3/30; C08K 5/5317; C08K 2003/3081; A61L 15/60; B01J 20/261; B01J 20/28047; B01J 2220/68; C08J 3/12; C08J 3/245; C08J 2333/02
USPC .......................................... 502/402
See application file for complete search history.

(56) References Cited

U.S. PATENT DOCUMENTS

| | | |
|---|---|---|
| 8,703,876 B2 | 4/2014 | Herfert et al. |
| 11,325,990 B2 | 5/2022 | Hartnagel et al. |

FOREIGN PATENT DOCUMENTS

| | | |
|---|---|---|
| EP | 2163302 A1 | 3/2010 |
| WO | WO-2011/113777 A1 | 9/2011 |
| WO | WO-2013/144026 A1 | 10/2013 |
| WO | WO-2013/144027 A1 | 10/2013 |

OTHER PUBLICATIONS

Graham, A.T., et al. (1998). "Commercial Processes for the Manufacture of Superabsorbent Polymers" In F. L. Buchholz (Ed.), *Modern Superabsorbent Polymer Technology* (pp. 69-114). New York, NY: John Wiley & Sons, Inc.
International Search Report for PCT Patent Application No. PCT/EP2017/069446, dated Nov. 7, 2017.

*Primary Examiner* — Edward M Johnson
(74) *Attorney, Agent, or Firm* — Element IP, PLC

(57) ABSTRACT

A process for producing superabsorbents, comprising polymerization of a monomer solution and thermal surface postcrosslinking, wherein the monomer solution comprises at least 0.75% by weight of a hydroxyphosphonic acid or salts thereof, calculated on the basis of the total amount of monomer used, and at least 0.09% by weight of aluminum cations, calculated on the basis of the total amount of polymer particles used, is added to the polymer particles before, during or after the thermal surface postcrosslinking.

17 Claims, No Drawings

METHOD FOR THE PRODUCTION OF SUPERABSORBERS

CROSS-REFERENCE TO RELATED APPLICATIONS

This is a divisional of U.S. application Ser. No. 16/321,638, filed Jan. 29, 2019, which is a U.S. national phase of International Application No. PCT/EP2017/069446, filed Aug. 1, 2017, which claims the benefit of European Application No. 16183579.8, filed Aug. 10, 2016.

DESCRIPTION

The present invention relates to a process for producing superabsorbents, comprising polymerization of a monomer solution and thermal surface postcrosslinking, wherein the monomer solution comprises at least 0.75% by weight of a hydroxyphosphonic acid, calculated on the basis of the total amount of monomer used, and at least 0.09% by weight of aluminum cations, calculated on the basis of the total amount of polymer particles used, is added to the polymer particles before, during or after the thermal surface postcrosslinking.

Superabsorbents are used to produce diapers, tampons, sanitary napkins and other hygiene articles, but also as water-retaining agents in market gardening. Superabsorbents are also referred to as water-absorbing polymers.

The production of superabsorbents is described in the monograph "Modern Superabsorbent Polymer Technology", F. L. Buchholz and A. T. Graham, Wiley-VCH, 1998, pages 71 to 103.

The properties of the superabsorbents can be adjusted, for example, via the amount of crosslinker used. With increasing amount of crosslinker, the centrifuge retention capacity (CRC) falls and the absorption under a pressure of 21.0 g/cm$^2$ (AUL0.3 psi) passes through a maximum.

To improve the performance properties, for example gel bed permeability (GBP) and absorption under a pressure of 49.2 g/cm$^2$ (AUL0.7 psi), superabsorbent particles are generally surface postcrosslinked. This increases the level of crosslinking of the particle surface, which can at least partly decouple the absorption under a pressure of 49.2 g/cm$^2$ (AUL0.7 psi) and the centrifuge retention capacity (CRC). This surface postcrosslinking can be performed in the aqueous gel phase. Preferably, however, dried, ground and sieved polymer particles (base polymer) are surface coated with a surface postcrosslinker and thermally surface postcrosslinked. Crosslinkers suitable for that purpose are compounds which can form covalent bonds to at least two carboxylate groups of the polymer particles.

WO 2011/113777 A1 describes the production of superabsorbents. This involves adding, during the polymerization or later, an inorganic phosphoric acid or salt thereof and an organic 2-hydroxy acid or salt thereof.

WO 2013/144026 A1 describes superabsorbents having surfaces that have been complexed with polyvalent metal ions and comprising a phosphonic acid derivative.

It was an object of the present invention to provide an improved process for producing color-stable superabsorbents having high gel bed permeability (GBP).

The object was achieved by a process for producing superabsorbents by polymerizing a monomer solution or suspension comprising a) at least one ethylenically unsaturated monomer which bears acid groups and may have been at least partly neutralized, b) at least one crosslinker, c) at least one initiator, d) optionally one or more ethylenically unsaturated monomers copolymerizable with the monomers mentioned under a) and e) optionally one or more water-soluble polymers, comprising the steps of i) polymerizing the monomer solution to give a polymer gel, ii) optionally comminuting the resulting polymer gel, drying the polymer gel, iv) grinding and classifying the dried polymer gel to give polymer particles, v) thermally surface postcrosslinking the classified polymer particles, vi) optionally reclassifying the surface postcrosslinked polymer particles, vii) optionally recycling polymer particles removed in step iv) upstream of step Hi) and viii) optionally recycling polymer particles removed in step vi) upstream of step Hi), which comprises adding to the monomer solution prior to step i) at least 0.75% by weight of a hydroxyphosphonic acid or salts thereof, calculated on the basis of the total amount of monomer a) used, and adding to the polymer particles between step iv) and step vi) at least 0.09% by weight of aluminum cations, calculated on the basis of the total amount of polymer particles used.

Salts of hydroxyphosphonic acid used are preferably alkali metal salts, more preferably sodium and potassium salts, most preferably sodium salts. The neutralizable protons of the hydroxyphosphonic acid may be entirely or partly replaced by any desired alkali metal cations.

In a preferred embodiment of the present invention, the surface postcrosslinked polymer particles are reclassified in step vi) and polymer particles removed in step vi) are recycled upstream of step Hi). The recycled polymer particles have a particle size of preferably less than 250 µm, more preferably of less than 200 µm, most preferably of less than 150 µm.

Preference is given to using 1-hydroxyethylidene-1,1'-diphosphonic acid as hydroxyphosphonic acid.

In a preferred embodiment of the present invention, aluminum cations are added prior to step v).

Preferably, the aluminum cation is used in the form of aluminum sulfate.

Added to the monomer solution is preferably at least 0.80% by weight, more preferably at least 0.85% by weight, most preferably at least 0.90% by weight, of a hydroxyphosphonic acid or salts thereof, calculated on the basis of the total amount of monomer a) used.

Added to the polymer particles between step iv) and step vi) is preferably at least 0.10% by weight, more preferably at least 0.11% by weight, most preferably at least 0.12% by weight, of aluminum cations, calculated on the basis of the total amount of polymer particles used.

The present invention is based on the finding that a high color stability and high gel bed permeability (GBP) can be achieved only with a relatively large amount of hydroxyphosphonic acid in the monomer solution and a relatively large amount of aluminum cations on the particle surface. The use of sulfate as counterion leads to a distinct increase in gel bed permeability (GBP).

In addition, it has been found that recycled surface postcrosslinked superabsorbents do not absorb hydroxyphosphonic acid from the monomer solution. If such superabsorbents ("fines") are recycled into the process, these polymer particles are not color-stable and lead to point discolorations. Point discolorations of this kind are perceived as being particularly troublesome. Surprisingly, this is also observed when the recycled superabsorbents have been coated with a hydroxyphosphonic acid at the polymer particle stage. It is possible that some polymer particles, especially the smaller polymer particles, are wetted only inadequately with the coating solution, if at all.

The production of the superabsorbents is described in detail hereinafter:

The superabsorbents are produced in step i) by polymerizing a monomer solution or suspension, and are typically water-insoluble.

The monomers a) are preferably water-soluble, i.e. their solubility in water at 23° C. is typically at least 1 g/100 g of water, preferably at least 5 g/100 g of water, more preferably at least 25 g/100 g of water and most preferably at least 35 g/100 g of water.

Suitable monomers a) are, for example, ethylenically unsaturated carboxylic acids, such as acrylic acid, methacrylic acid and itaconic acid. Particularly preferred monomers are acrylic acid and methacrylic acid. Very particular preference is given to acrylic acid.

Further suitable monomers a) are, for example, ethylenically unsaturated sulfonic acids, such as styrenesulfonic acid and 2-acrylamido-2-methylpropanesulfonic acid (AMPS).

Impurities can have a considerable influence on the polymerization. The raw materials used should therefore have a maximum purity. It is therefore often advantageous to specially purify the monomers a). Suitable purification processes are described, for example, in WO 02/055469 A1, WO 03/078378 A1 and WO 2004/035514 A1. A suitable monomer a) is, for example, an acrylic acid purified according to WO 2004/035514 A1 and comprising 99.8460% by weight of acrylic acid, 0.0950% by weight of acetic acid, 0.0332% by weight of water, 0.0203% by weight of propionic acid, 0.0001% by weight of furfurals, 0.0001% by weight of maleic anhydride, 0.0003% by weight of diacrylic acid and 0.0050% by weight of hydroquinone monomethyl ether.

The proportion of acrylic acid and/or salts thereof in the total amount of monomers a) is preferably at least 50 mol %, more preferably at least 90 mol %, most preferably at least 95 mol %.

The monomers a) typically comprise polymerization inhibitors, preferably hydroquinone monoethers, as storage stabilizers.

The monomer solution comprises preferably up to 250 ppm by weight, preferably at most 130 ppm by weight, more preferably at most 70 ppm by weight, and preferably at least 10 ppm by weight, more preferably at least 30 ppm by weight and especially around 50 ppm by weight, of hydroquinone monoether, based in each case on the unneutralized monomer a). For example, the monomer solution can be prepared by using an ethylenically unsaturated monomer bearing acid groups with an appropriate content of hydroquinone monoether.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized free-radically into the polymer chain, and functional groups which can form covalent bonds with the acid groups of the monomer a). In addition, polyvalent metal salts which can form coordinate bonds with at least two acid groups of the monomer a) are also suitable as crosslinkers b).

Crosslinkers b) are preferably compounds having at least two polymerizable groups which can be polymerized free-radically into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 03/104299 A1, WO 03/104300 A1, WO 03/104301 A1 and DE 103 31 450 A1, mixed acrylates which, as well as acrylate groups, comprise further ethylenically unsaturated groups, as described in DE 103 31 456 A1 and DE 103 55 401 A1, or crosslinker mixtures, as described, for example, in DE 195 43 368 A1, DE 196 46 484 A1, WO 90/15830 A1 and WO 02/032962 A2.

Preferred crosslinkers b) are pentaerythrityl triallyl ether, tetraallyloxyethane, methylenebismethacrylamide, 15-tuply ethoxylated trimethylolpropane triacrylate, polyethylene glycol diacrylate, trimethylolpropane triacrylate and triallylamine.

Very particularly preferred crosslinkers b) are the polyethoxylated and/or propoxylated glycerols which have been esterified with acrylic acid or methacrylic acid to give di- or triacrylates, as described, for example, in WO 03/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol, especially the triacrylate of 3-tuply ethoxylated glycerol.

The amount of crosslinker b) is preferably 0.25% to 1.5% by weight, more preferably 0.3% to 1.2% by weight and most preferably 0.4% to 0.8% by weight, calculated in each case on the basis of the total amount of monomer a) used. With rising crosslinker content, centrifuge retention capacity (CRC) falls and the absorption under a pressure of 21.0 g/cm$^2$ passes through a maximum.

Initiators c) used may be all compounds which generate free radicals under the polymerization conditions, for example thermal initiators, redox initiators or photoinitiators. Suitable redox initiators are sodium peroxodisulfate/ascorbic acid, hydrogen peroxide/ascorbic acid, sodium peroxodisulfate/sodium bisulfite and hydrogen peroxide/sodium bisulfite. Preference is given to using mixtures of thermal initiators and redox initiators, such as sodium peroxodisulfate/hydrogen peroxide/ascorbic acid. The reducing component used is preferably the disodium salt of 2-hydroxy-2-sulfonatoacetic acid or a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

Ethylenically unsaturated monomers d) copolymerizable with the ethylenically unsaturated monomers a) bearing acid groups are, for example, acrylamide, methacrylamide, hydroxyethyl acrylate, hydroxyethyl methacrylate, dimethylaminoethyl methacrylate, dimethylaminoethyl acrylate, dimethylaminopropyl acrylate, diethylaminopropyl acrylate, dimethylaminoethyl methacrylate, diethylaminoethyl methacrylate.

The water-soluble polymers e) used may be polyvinyl alcohol, polyvinylpyrrolidone, starch, starch derivatives, modified cellulose, such as methyl cellulose or hydroxyethyl cellulose, gelatin, polyglycols or polyacrylic acids, preferably starch, starch derivatives and modified cellulose.

Typically, an aqueous monomer solution is used. The water content of the monomer solution is preferably from 40% to 75% by weight, more preferably from 45% to 70% by weight and most preferably from 50% to 65% by weight. It is also possible to use monomer suspensions, i.e. monomer solutions with solubility-exceeding monomer a), for example sodium acrylate. As the water content rises, the energy expenditure in the subsequent drying rises and, as the water content falls, the heat of polymerization can only be removed inadequately.

For optimal action, the preferred polymerization inhibitors require dissolved oxygen. The monomer solution can therefore be freed of dissolved oxygen before the polymerization by inertization, i.e. flowing an inert gas through, preferably nitrogen or carbon dioxide. The oxygen content of the monomer solution is preferably lowered before the polymerization to less than 1 ppm by weight, more preferably to less than 0.5 ppm by weight, most preferably to less than 0.1 ppm by weight.

Suitable reactors for the polymerization in step i) are, for example, kneading reactors or belt reactors. In the kneader, the polymer gel formed in the polymerization of an aqueous monomer solution or suspension is comminuted continuously by, for example, contrarotatory stirrer shafts, as described in WO 2001/038402 A1. Polymerization on a belt is described, for example, in DE 38 25 366 A1 and U.S. Pat. No. 6,241,928. Polymerization in a belt reactor forms a polymer gel which has to be comminuted in a further step, step ii), for example in an extruder or kneader.

To improve the drying properties, the comminuted polymer gel obtained by means of a kneader can additionally be extruded in step ii).

The acid groups of the resulting polymer gels have typically been partly neutralized. Neutralization is preferably carried out at the monomer stage. This is typically accomplished by mixing in the neutralizing agent as an aqueous solution or else preferably as a solid. The degree of neutralization is preferably from 25 to 85 mol %, more preferably from 30 to 80 mol % and most preferably from 40 to 75 mol %, for which the customary neutralizing agents can be used, preferably alkali metal hydroxides, alkali metal oxides, alkali metal carbonates or alkali metal hydrogencarbonates and also mixtures thereof. Instead of alkali metal salts, it is also possible to use ammonium salts. Particularly preferred alkali metals are sodium and potassium, but very particular preference is given to sodium hydroxide, sodium carbonate or sodium hydrogencarbonate and also mixtures thereof. Solid carbonates and hydrogencarbonates can also be introduced here in encapsulated form, preferably into the monomer solution directly prior to the polymerization, into the polymer gel during or after the polymerization and prior to the drying thereof. The encapsulation is effected by coating of the surface with an insoluble or only gradually soluble material (for example by means of film-forming polymers, of inert inorganic materials or of fusible organic materials) which delays the dissolution and reaction of the solid carbonate or hydrogencarbonate to such a degree that carbon dioxide is not released until during the drying and the superabsorbent formed has high internal porosity.

Optionally, a surfactant can be added to the monomer solution before or during the polymerization and the monomer solution can then be foamed before or during the polymerization with an inert gas or water vapor or by vigorous stirring. The surfactant may be anionic, cationic, zwitterionic or else nonionic. Preference is given to using a skin-friendly surfactant.

The polymer gel is then dried with an air circulation belt drier in step Hi) until the residual moisture content is preferably 0.5 to 10% by weight, more preferably 1 to 6% by weight and most preferably 1.5 to 4% by weight, the residual moisture content being determined by EDANA recommended test method No. WSP 230.2-05 "Mass Loss Upon Heating". In the case of too high a residual moisture content, the dried polymer gel has too low a glass transition temperature $T_g$ and can be processed further only with difficulty. In the case of too low a residual moisture content, the dried polymer gel is too brittle and, in the subsequent comminution steps, undesirably large amounts of polymer particles with an excessively low particle size are obtained ("fines"). The solids content of the polymer gel before the drying is preferably from 25% to 90% by weight, more preferably from 35% to 70% by weight, most preferably from 40% to 60% by weight. Subsequently, the dried polymer gel is crushed and optionally coarsely comminuted.

Thereafter, the dried polymer gel is ground and classified in step iv), and the apparatus used for grinding may typically be single or multistage roll mills, preferably two- or three-stage roll mills, pin mills, hammer mills or vibratory mills.

The average particle size of the polymer particles removed as the product fraction in step xii) is preferably from 150 to 850 μm, more preferably from 250 to 600 μm, very particularly from 300 to 500 μm. The average particle size of the product fraction may be determined by means of EDANA recommended test method No. WSP 220.2-05 "Particle Size Distribution", where the proportions by mass of the screen fractions are plotted in cumulated form and the average particle size is determined graphically. The average particle size here is the value of the mesh size which arises for a cumulative 50% by weight.

The proportion of polymer particles having a particle size of greater than 150 μm is preferably at least 90% by weight, more preferably at least 95% by weight, most preferably at least 98% by weight.

Polymer particles with too small a particle size lower the gel bed permeability (GBP). The proportion of excessively small polymer particles ("fines") should therefore be small.

Excessively small polymer particles are therefore typically removed and recycled into the process, preferably before, during or immediately after the polymerization in step i), i.e. prior to the drying of the polymer gel in step iii). The excessively small polymer particles can be moistened with water and/or aqueous surfactant before or during the recycling.

It is also possible to remove excessively small polymer particles in later process steps, for example after the surface postcrosslinking in step v) or another coating step. In this case, the excessively small polymer particles recycled are surface postcrosslinked or coated in another way, for example with fumed silica.

If a kneading reactor is used for polymerization, the excessively small polymer particles are preferably added in step i) during the last third of the polymerization. However, it is also possible to incorporate the excessively small polymer particles into the polymer gel in a step ii) downstream of the polymerization reactor, for example in a kneader or extruder.

If the excessively small polymer particles are added at a very early stage, for example actually to the monomer solution, this lowers the centrifuge retention capacity (CRC)

of the resulting polymer particles. However, this can be compensated, for example, by adjusting the amount of crosslinker b) used.

The proportion of polymer particles having a particle size of at most 850 µm is preferably at least 90% by weight, more preferably at least 95% by weight, most preferably at least 98% by weight.

The proportion of polymer particles having a particle size of at most 600 µm is preferably at least 90% by weight, more preferably at least 95% by weight, most preferably at least 98% by weight.

Polymer particles of excessively large particle size lower the free swell rate. The proportion of excessively large polymer particles should therefore likewise be low. Excessively large polymer particles are therefore typically removed and recycled into the grinding.

To further improve the properties, the polymer particles can be thermally surface postcrosslinked in step v). Suitable surface postcrosslinkers are compounds which comprise groups which can form covalent bonds with at least two carboxylate groups of the polymer particles. Suitable compounds are, for example, polyfunctional amines, polyfunctional amido amines, polyfunctional epoxides, as described in EP 0 083 022 A2, EP 0 543 303 A1 and EP 0 937 736 A2, di- or polyfunctional alcohols, as described in DE 33 14 019 A1, DE 35 23 617 A1 and EP 0 450 922 A2, or β-hydroxyalkylamides, as described in DE 102 04 938 A1 and U.S. Pat. No. 6,239,230.

Additionally described as suitable surface postcrosslinkers are cyclic carbonates in DE 40 20 780 C1, 2-oxazolidinone and derivatives thereof, such as 2-hydroxyethyl-2-oxazolidinone, in DE 198 07 502 A1, bis- and poly-2-oxazolidinones in DE 198 07 992 C1, 2-oxotetrahydro-1,3-oxazine and derivatives thereof in DE 198 54 573 A1, N-acyl-2-oxazolidinones in DE 198 54 574 A1, cyclic ureas in DE 102 04 937 A1, bicyclic amido acetals in DE 103 34 584 A1, oxetanes and cyclic ureas in EP 1 199 327 A2 and morpholine-2,3-dione and derivatives thereof in WO 03/031482 A1.

Preferred surface postcrosslinkers are ethylene carbonate, ethylene glycol diglycidyl ether, reaction products of polyamides with epichlorohydrin and mixtures of propylene glycol and 1,4-butanediol.

Very particularly preferred surface postcrosslinkers are 2-hydroxyethyl-2-oxazolidinone, 2-oxazolidinone and 1,3-propanediol.

In addition, it is also possible to use surface postcrosslinkers which comprise additional polymerizable ethylenically unsaturated groups, as described in DE 37 13 601 A1.

The amount of surface postcrosslinker is preferably 0.001% to 3% by weight, more preferably 0.02% to 1% by weight and most preferably 0.05% to 0.2% by weight, based in each case on the polymer particles.

The surface postcrosslinking is typically performed in such a way that a solution of the surface postcrosslinker is sprayed onto the dried polymer particles. After the spray application, the polymer particles coated with surface postcrosslinker are surface postcrosslinked and dried, and the surface postcrosslinking reaction can take place both before and during the drying.

The spray application of a solution of the surface postcrosslinker is preferably performed in mixers with moving mixing tools, such as screw mixers, disk mixers and paddle mixers. Particular preference is given to horizontal mixers such as paddle mixers, very particular preference to vertical mixers. The distinction between horizontal mixers and vertical mixers is made by the position of the mixing shaft, i.e. horizontal mixers have a horizontally mounted mixing shaft and vertical mixers a vertically mounted mixing shaft. Suitable mixers are, for example, horizontal Pflugschar® plowshare mixers (Gebr. Lödige Maschinenbau GmbH; Paderborn; Germany), Vrieco-Nauta continuous mixers (Hosokawa Micron BV; Doetinchem; the Netherlands), Processall Mixmill mixers (Processall Incorporated; Cincinnati; USA) and Schugi Flexomix® (Hosokawa Micron BV; Doetinchem; the Netherlands). However, it is also possible to spray on the surface postcrosslinker solution in a fluidized bed.

The surface postcrosslinkers are typically used in the form of an aqueous solution. The penetration depth of the surface postcrosslinker into the polymer particles can be adjusted via the content of nonaqueous solvent and total amount of solvent.

When exclusively water is used as the solvent, a surfactant is advantageously added. This improves the wetting characteristics and reduces the tendency to form lumps. However, preference is given to using solvent mixtures, for example isopropanol/water, 1,3-propanediol/water and propylene glycol/water, where the mixing ratio in terms of mass is preferably from 20:80 to 40:60.

The surface postcrosslinking is preferably performed in contact driers, more preferably shovel driers, most preferably disk driers. Suitable driers are, for example, Hosokawa Bepex® Horizontal Paddle Dryer (Hosokawa Micron GmbH; Leingarten; Germany), Hosokawa Bepex® Disc Dryer (Hosokawa Micron GmbH; Leingarten; Germany), Holo-Elite® driers (Metso Minerals Industries Inc.; Danville; USA) and Nara Paddle Dryer (NARA Machinery Europe; Frechen; Germany). Moreover, fluidized bed driers may also be used.

The surface postcrosslinking can be effected in the mixer itself, by heating the jacket or blowing in warm air. Equally suitable is a downstream drier, for example a shelf drier, a rotary tube oven or a heatable screw. It is particularly advantageous to effect mixing and thermal surface postcrosslinking in a fluidized bed drier.

Preferred reaction temperatures are in the range of 100 to 250° C., preferably 120 to 220° C., more preferably 130 to 210° C., most preferably 150 to 200° C. The preferred dwell time at this temperature is preferably at least 10 minutes, more preferably at least 20 minutes, most preferably at least 30 minutes, and typically at most 60 minutes.

In a preferred embodiment of the present invention, the polymer particles are cooled after the surface postcrosslinking. The cooling is preferably performed in contact coolers, more preferably paddle coolers and most preferably disk coolers. Suitable coolers are, for example, Hosokawa Bepex® Horizontal Paddle Cooler (Hosokawa Micron GmbH; Leingarten; Germany), Hosokawa Bepex® Disc Cooler (Hosokawa Micron GmbH; Leingarten; Germany), Holo-Elite® coolers (Metso Minerals Industries Inc.; Danville; USA) and Nara Paddle Cooler (NARA Machinery Europe; Frechen; Germany). Moreover, fluidized bed coolers may also be used.

In the cooler, the polymer particles are cooled to preferably 40 to 90° C., more preferably 45 to 80° C., most preferably 50 to 70° C.

Subsequently, the surface postcrosslinked polymer particles can be classified again, with excessively small and/or excessively large polymer particles being removed and recycled into the process.

To further improve the properties, the surface postcrosslinked polymer particles can be coated or remoisturized.

The remoisturizing is preferably performed at 40 to 120° C., more preferably at 50 to 110° C., most preferably at 60 to 100° C. At excessively low temperatures the polymer particles tend to form lumps, and at higher temperatures water already evaporates to a noticeable degree. The amount of water used for remoisturizing is preferably from 1% to 10% by weight, more preferably from 2% to 8% by weight and most preferably from 3% to 5% by weight. The remoisturizing increases the mechanical stability of the polymer particles and reduces their tendency to static charging. The remoisturizing is advantageously performed in the cooler after the thermal surface postcrosslinking.

Suitable coatings for improving the free swell rate and the gel bed permeability (GBP) are, for example, inorganic inert substances, such as water-insoluble metal salts, organic polymers, cationic polymers and di- or polyvalent metal cations. Suitable coatings for dust binding are, for example, polyols. Suitable coatings for counteracting the undesired caking tendency of the polymer particles are, for example, fumed silica, such as Aerosil® 200, and surfactants, such as Span® 20. Suitable coatings for dust binding, for reducing the tendency to caking and for increasing the mechanical stability are polymer dispersions as described in EP 0 703 265 B1, and waxes as described in U.S. Pat. No. 5,840,321.

The present invention further provides the superabsorbents produced by the process of the invention, where the superabsorbent particles have a centrifuge retention capacity of at least 25 g/g, an absorption under a pressure of 49.2 g/cm$^2$ of at least 15 g/g, a gel bed permeability of at least 60 darcies, and the superabsorbent particles, after storage at a temperature of 70° C. and a relative humidity of 80% for 14 days, have an L value of at least 67, an a value of less than 7.0 and a b value of less than 14.5.

The superabsorbent particles of the invention have high color stability even in a mixture with cellulose as typically exists in diapers. By contrast, superabsorbent particles in which the color stabilizer has merely been applied to the surface thereof have distinctly lower color stability when mixed with cellulose.

The superabsorbent particles produced by the process of the invention have a centrifuge retention capacity (CRC) of preferably at least 26 g/g, more preferably at least 27 g/g, most preferably at least 28 g/g. The centrifuge retention capacity (CRC) of the superabsorbent particles is typically less than 60 g/g.

The superabsorbent particles produced by the process of the invention have an absorption under a pressure of 49.2 g/cm$^2$ (AUL0.7 psi) of preferably at least 16 g/g, more preferably at least 17 g/g, most preferably at least 18 g/g. The absorption under a pressure of 49.2 g/cm$^2$ (AUL0.7 psi) of the superabsorbent particles is typically less than 35 g/g.

The superabsorbent particles produced by the process of the invention have a gel bed permeability (GBP) of preferably at least 65 darcies, more preferably at least 70 darcies, most preferably at least 75 darcies. The gel bed permeability (GBP) of the superabsorbent particles is typically less than 400 darcies.

The superabsorbent particles produced by the process of the invention, after storage at a temperature of 70° C. and a relative humidity of 80% for 14 days, have an L value of preferably at least 68, more preferably at least 69, most preferably at least 70.

The superabsorbent particles produced by the process of the invention, after storage at a temperature of 70° C. and a relative humidity of 80% for 14 days, preferably have an a value of less than 6.6 and a b value of less than 14.0, more preferably an a value of less than 6.2 and a b value of less than 13.5, most preferably an a value of less than 5.8 and a b value of less than 13.0.

Methods:

The standard test methods described hereinafter and designated "WSP" are described in: "Standard Test Methods for the Nonwovens Industry", 2005 edition, published jointly by the Worldwide Strategic Partners EDANA (Avenue Eugene Plasky, 157, 1030 Brussels, Belgium, www.edana.org) and INDA (1100 Crescent Green, Suite 115, Cary, N.C. 27518, USA, www.inda.org). This publication is obtainable both from EDANA and from INDA.

The measurements should, unless stated otherwise, be conducted at an ambient temperature of 23±2° C. and a relative air humidity of 50±10%. The water-absorbing polymer particles are mixed thoroughly before the measurement.

Centrifuge Retention Capacity

The centrifuge retention capacity (CRC) is determined by EDANA recommended test method No. WSP 241.2-05 "Fluid Retention Capacity in Saline, After Centrifugation".

Absorption Under a Pressure of 21.0 g/Cm$^2$ (Absorption Under Load)

The absorption under a pressure of 21.0 g/cm$^2$ (AUL0.3 psi) of the water-absorbing polymer particles is determined by EDANA recommended test method No. WSP 242.2-05 "Absorption Under Pressure, Gravimetric Determination".

Absorption Under a Pressure of 49.2 g/Cm$^2$ (Absorption Under Load)

The absorption under a pressure of 49.2 g/cm$^2$ (AUL0.7 psi) is determined analogously to EDANA recommended test method No. WSP 242.2-05 "Absorption Under Pressure, Gravimetric Determination", except that a pressure of 49.2 g/cm$^2$ (AUL0.7 psi) is established rather than a pressure of 21.0 g/cm$^2$ (AUL0.3 psi).

Gel Bed Permeability

The gel bed permeability (GBP) of a swollen gel layer under a pressure of 0.3 psi (2070 Pa) is, as described in US 2005/0256757 (paragraphs [0061] and [0075]), determined as the gel bed permeability of a swollen gel layer of water-absorbing polymer particles.

CIE Color Number (L, a, b)

The color analysis is carried out according to the CIELAB method (Hunterlab, volume 8, 1996, book 7, pages 1 to 4) with a "LabScan XE S/N LX17309" colorimeter (HunterLab, Reston, US). This method describes the colors via the coordinates L, a and b of a three-dimensional system. L indicates the brightness, where L=0 means black and L=100 white. The values of a and b indicate the positions of the color on the red/green and yellow/blue color axes respectively, where +a represents red, −a represents green, +b represents yellow and −b represents blue. The HC60 is calculated by the formula HC60=L-3b.

The color measurement corresponds to the three-area method according to DIN 5033-6.

EXAMPLES

Example 1

A monomer solution which is composed of 406.8 g of acrylic add, 4271.4 g of aqueous sodium acrylate solution (37.3% strength by weight), 130.4 g of water and 5.86 g of 3-tuply ethoxylated glycerol triacrylate (purity about 85% by weight) and has been freed of atmospheric oxygen with nitrogen gas for 30 minutes was polymerized in an LUK 8.0 K2 polymerization reactor having two axially parallel shafts (Coperion Werner & Pfleiderer GmbH & Co, KG; Stuttgart, Germany). Additionally added to the monomer solution were 77.29 g of an aqueous solution of the disodium salt of 1-hydroxyethylidene-1,1-diphosphonic acid (20% strength by weight). The polymerization was initiated by adding 15.84 q of aqueous sodium peroxodisulfate solution (15% strength by weight), 141 g of aqueous hydrogen peroxide (1% strength by weight) and 9112 g of aqueous ascorbic acid solution (0.5% strength by weight). The polymerization had ended after about 30 minutes. The resulting polymer gel was ground three times with the aid of a commercial meat grinder with a 6 mm die plate, and dried in a laboratory drying cabinet at 175° C. for 90 minutes. The dried polymer was ground and sieved to a particle size of 150 to 710 µm. The base polymer thus produced had a centrifuge retention capacity (CRC) of 38 g/g.

For surface postcrosslinkinq, 1000 g of base polymer were coated in an M5R plowshare mixer (Gebrüder Lödige Maschinenbau GmbH; Paderborn; Germany) at 23° C. and a shaft speed of 200 revolutions per minute by means of two two-phase spray nozzles with the following solutions:
Solution 1: 0.50 g of N-(2-hydroxyethyl)-2-oxazolidinone
  0.50 g of propane-1,3-diol
  33.10 g of aqueous aluminum sulfate solution (26.8% strength by weight)
Solution 11: 10.0 g of isopropanol After the spray application of the two solutions, the temperature was increased to 195° C. and the reaction mixture was held at this temperature and a shaft speed of 60 revolutions per minute for 75 minutes. Subsequently, the reaction mixture was resieved at 23° C. to a particle size of 150 to 710 µm.

The superabsorbent particles obtained were analyzed. To determine color stability, the superabsorbent particles were stored at 70° C. and a relative humidity of 80% for 14 days. The results are compiled in table 1.

Example 2 (Comparative Example)

The procedure was as in example 1. Rather than 77.29 g of an aqueous solution of the disodium salt of 1-hydroxyethylidene-1,1-diphosphonic acid (20% strength by weight), only 36.61 g of an aqueous solution of the disodium salt of 1-hydroxyethylidene-1,1-diphosphonic acid (20% strength by weight) were added to the monomer solution.

The superabsorbent particles obtained were analyzed. To determine color stability, the superabsorbent particles were stored at 70° C. and a relative humidity of 80% for 14 days. The results are compiled in table 1.

Example 3 (Comparative Example)

The procedure was as in example 1. Surface postcrosslinking was accomplished using, rather than 42.90 g of aqueous aluminum sulfate solution (26.8% strength by weight), only 11.10 g of aqueous aluminum sulfate solution (26.8% strength by weight).

The superabsorbent particles obtained were analyzed. To determine color stability, the superabsorbent particles were stored at 70° C. and a relative humidity of 80% for 14 days. The results are compiled in table 1.

Example 4 (Comparative Example)

The procedure was as in example 1. The monomer solution did not comprise any disodium salt of 1-hydroxyethylidene-11-diphosphonic acid. Instead, 15.46 g of the disodium salt of 2-hydroxy-2-sulfonatoacetic acid were added to the monomer solution.

During the polymerization, the polymer gel formed wound around the shafts of the polymerization reactor. The experiment had to be stopped.

Example 5 (Comparative Example)

The procedure was as in example 1. The monomer solution did not comprise any disodium salt of 1-hydroxyethylidene-11-diphosphonic acid.

The superabsorbent particles obtained were analyzed. To determine color stability, the superabsorbent particles were stored at 70° C. and a relative humidity of 80% for 14 days. The results are compiled in table 1.

Example 6

The procedure was as in example 1. No aluminum sulfate was used for surface postcrosslinking. Instead, 80.8 g of aqueous aluminum trilactate solution (18.9% strength by weight) were used.

The superabsorbent particles obtained were analyzed. To determine color stability, the superabsorbent particles were stored at 70° C. and a relative humidity of 80% for 14 days. The results are compiled in table 1.

TABLE 1

| Ex. | Monomer solution | SXL | CRC [g/g] | AUL0.7psi [g/g] | GBP [darcies] | L | a | b |
|---|---|---|---|---|---|---|---|---|
| 1 | 9500 ppm Cublen | 1500 ppm $Al^{3+}$ (as sulfate) | 29.8 | 21.4 | 109 | 74 | 5.3 | 12 |
| 2*) | 4500 ppm Cublen | 1500 ppm $Al^{3+}$ (as sulfate) | 30.4 | 21.5 | 101 | 63 | 7.3 | 15 |
| 3*) | 9500 ppm Cublen | 500 ppm $Al^{3+}$ (as sulfate) | 31.1 | 23.3 | 26 | 85 | 0.9 | 8.6 |
| 4*) | 9500 ppm Blancolen | **) | — | — | — | — | — | — |
| 5*) | No Cublen | 1500 ppm $Al^{3+}$ (as sulfate) | 29.9 | 20.6 | 118 | 50 | 9.1 | 16.7 |
| 6*) | 9500 ppm Cublen | 1500 ppm $Al^{3+}$ (as lactate) | 29.3 | 25.3 | 17 | 79 | 3.7 | 11 |

SXL: surface postcrosslinking
Cublen: disodium salt of 1-hydroxyethylidene-1,1-diphosphonic acid
Blancolen: disodium salt of 2-hydroxy-2-sulfonatoacetic acid
*) comparative experiment
**) not possible, polymerization stopped The results of examples 1 to 3 show that superabsorbents having high color stability and high gel bed permeability (GBP) are obtained only with a large amount of hydroxyphosphonic acid (Cublen) and a large amount of aluminum cations.

Example 4 shows that 2-hydroxysulfonic acids (Blancolen), in the amounts in the monomer solution that are necessary for color stabilization, interfere in the polymerization.

Examples 1 and 6 show the advantages of sulfate over lactate as counterion.

Example 7

By mixing water, aqueous sodium hydroxide solution and acrylic acid, a 43.0% strength by weight acrylic acid/sodium acrylate solution was prepared. The degree of neutralization of the monomer solution thus prepared was 72.0 mol %.

The monomer solution was degassed with nitrogen at about 23° C. The polyethylenically unsaturated crosslinker used was 3-tuply ethoxylated glyceryl triacrylate (purity about 85% by weight). The use amount of 3-tuply ethoxylated glycerol triacrylate, calculated on the basis of the amount of acrylic acid used, was 0.16% by weight.

Additionally added to the monomer solution was a 20% by weight aqueous solution of the disodium salt of 1-hydroxyethylidene-1,1-diphosphonic acid. The use amount of disodium salt of 1-hydroxyethylidene-1,1-diphosphonic acid, calculated on the basis of the amount of acrylic acid used, was 0.30% by weight.

To initiate the free-radical polymerization, the following components were used: hydrogen peroxide (0.002% by weight of a 1.0% by weight aqueous solution), sodium peroxodisulfate (0.15% by weight of a 15% by weight aqueous solution), and ascorbic acid (0.01% by weight of a 0.5% by weight aqueous solution). The percentages by weight were calculated based on the total amount of acrylic acid used.

The individual components were metered continuously into a List ORP 10 kneader reactor (List AG, Arisdorf, Switzerland). The throughput of the monomer solution was 40 kg/h.

The reaction solution had a feed temperature of about 23° C. The dwell time of the reaction mixture in the reactor was about 15 minutes. After polymerization and gel comminution, 1 kg of aqueous polymer gel in each case was applied to drying sheets with a base of 300 μm sieve mesh and dried in an air circulation drying cabinet at 175° C. for 60 minutes. The dried polymer gel was ground and classified by means of a roll mill.

To determine color stability, the superabsorbent particles were stored at 70° C. and a relative humidity of 80% for 14 days. The results are compiled in table 2.

Example 8

The procedure was as in example 7. In the first third of the reactor, 0.86 kg/h of superabsorbent with a particle size of less than 150 μm was additionally added. The added superabsorbent particles had been thermally surface postcrosslinked and did not comprise any disodium salt of 1-hydroxyethylidene-1,1-diphosphonic acid.

To determine color stability, the superabsorbent particles were stored at 70° C. and a relative humidity of 80% for 14 days. The results are compiled in table 2.

Example 9

The procedure was as in example 7. In the first third of the reactor, 1.72 kg/h of superabsorbent with a particle size of less than 150 μm were additionally added. The added superabsorbent particles had been thermally surface postcrosslinked and did not comprise any disodium salt of 1-hydroxyethylidene-1,1-diphosphonic acid.

To determine color stability, the superabsorbent particles were stored at 70° C. and a relative humidity of 80% for 14 days. The results are compiled in table 2.

Example 10

The procedure was as in example 7. In the first third of the reactor, 2.58 kg/h of superabsorbent with a particle size of less than 150 μm were additionally added. The added superabsorbent particles had been thermally surface postcrosslinked and did not comprise any disodium salt of 1-hydroxyethylidene-1,1-diphosphonic acid.

To determine color stability, the superabsorbent particles were stored at 70° C. and a relative humidity of 80% for 14 days. The results are compiled in table 2.

Example 11

The procedure was as in example 7. In the first third of the reactor, 3.44 kg/h of superabsorbent with a particle size of less than 150 μm were additionally added. The added superabsorbent particles had been thermally surface postcrosslinked and did not comprise any disodium salt of 1-hydroxyethylidene-1,1-diphosphonic acid.

To determine color stability, the superabsorbent particles were stored at 70° C. and a relative humidity of 80% for 14 days. The results are compiled in table 2.

TABLE 2

| Ex. | Superabsorbent added (calculated based on polymer produced) | Discolorations |
| --- | --- | --- |
| 7 | none | + |
| 8 | 5% by weight | − |
| 9 | 10% by weight | − |
| 10 | 15% by weight | −− |
| 11 | 20% by weight | −−− |

+ No visible point discolorations
− Few visible point discolorations
−− Distinct, visible point discolorations
−−− Very distinct, visible point discolorations The results of examples 7 to 11 show that the thermally surface postcrosslinked superabsorbent particles no longer absorb any disodium salt of 1-hydroxyethylidene-1,1-diphosphonic acid and do not become discolored during storage. The point discolorations increase with the amount of added superabsorbent.

The invention claimed is:

1. Superabsorbent particles having a centrifuge retention capacity of at least 25 g/g, an absorption under a pressure of 49.2 g/cm$^2$ of at least 15 g/g, a gel bed permeability of at least 60 darcies, and the superabsorbent particles, after storage at a temperature of 70° C. and a relative humidity of 80% for 14 days, have an L value of at least 67, an a value of less than 7.0 and a b value of less than 14.5, wherein the particles are prepared by polymerizing a monomer solution or suspension comprising
   a) at least one ethylenically unsaturated monomer which bears an acid group and optionally is at least partly neutralized,
   b) at least one crosslinker,
   c) at least one initiator, d) optionally one or more ethylenically unsaturated monomer copolymerizable with the monomer a) and
e) optionally one or more water-soluble polymer, comprising
  i) polymerizing the monomer solution to give a polymer gel,
  ii) optionally comminuting the resulting polymer gel,
  iii) drying the polymer gel,
  iv) grinding and classifying the dried polymer gel to give polymer particles,
  v) thermally surface postcrosslinking the classified polymer particles,
  vi) optionally reclassifying the surface postcrosslinked polymer particles,
  vii) optionally recycling polymer particles removed in step iv) upstream of step iii) and
  viii) optionally recycling polymer particles removed in step vi) upstream of step iii),
which comprises adding to the monomer solution prior to step i) at least 0.75% by weight of a hydroxyphosphonic acid or salts thereof, calculated on the basis of the total amount of monomer a) used, and adding to the polymer particles between step iv) and step vi) at least 0.09% by weight of aluminum cations, calculated on the basis of the total amount of polymer particles used.

2. Superabsorbent particles according to claim 1, wherein the centrifuge retention capacity is at least 28 g/g.

3. Superabsorbent particles according to claim 1, wherein the absorption under a pressure of 49.2 g/cm$^2$ is at least 18 g/g.

4. Superabsorbent particles according to claim 1, wherein the gel bed permeability is at least 75 darcies.

5. Superabsorbent particles according to claim 1, wherein the superabsorbent particles after storage at a temperature of 70° C. and a relative humidity of 80% for 14 days, have an L value of at least 70.

6. Superabsorbent particles according to claim 1, wherein the superabsorbent particles after storage at a temperature of 70° C. and a relative humidity of 80% for 14 days, have an a value of less than 5.8 and a b value of less than 13.0.

7. Superabsorbent particles according to claim 2, wherein the absorption under a pressure of 49.2 g/cm$^2$ is at least 18 g/g.

8. Superabsorbent particles according to claim 7, wherein the gel bed permeability is at least 75 darcies.

9. Superabsorbent particles according to claim 8, wherein the superabsorbent particles after storage at a temperature of 70° C. and a relative humidity of 80% for 14 days, have an L value of at least 70.

10. Superabsorbent particles according to claim 9, wherein the superabsorbent particles after storage at a temperature of 70° C. and a relative humidity of 80% for 14 days, have an a value of less than 5.8 and a b value of less than 13.0.

11. Superabsorbent particles according to claim 1, wherein the polymer particles removed in step vi) and recycled upstream of step iii) have a particle size of less than 150 μm.

12. Superabsorbent particles according to claim 1, wherein the hydroxyphosphonic acid is 1-hydroxyethylidene-1,1'-diphosphonic acid.

13. Superabsorbent particles according to claim 1, wherein the aluminum cations are added prior to step v).

14. Superabsorbent particles according to claim 1, wherein the aluminum cation is used in the form of aluminum sulfate.

15. Superabsorbent particles according to claim 1, wherein at least 0.8% by weight of a hydroxyphosphonic acid or salts thereof, calculated on the basis of the total amount of monomer a) used, is added to the monomer solution prior to step i).

16. Superabsorbent particles according to claim 1, wherein at least 0.85% by weight of a hydroxyphosphonic acid or salts thereof, calculated on the basis of the total amount of monomer a) used, is added to the monomer solution prior to step i).

17. Superabsorbent particles according to claim 1, wherein at least 0.1% by weight of aluminum cations, calculated on the basis of the total amount of polymer particles used, is added to the polymer particles after step iv).

* * * * *